(12) United States Patent
Bao et al.

(10) Patent No.: US 6,575,013 B2
(45) Date of Patent: Jun. 10, 2003

(54) ELECTRONIC ODOR SENSOR

(75) Inventors: Zhenan Bao, North Plainfield, NJ (US); Brian Keith Crone, Zurich (CH); Ananth Dodabalapur, Millington, NJ (US); Alan Gelperin, Princeton, NJ (US); Howard Edan Katz, Summit, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/793,642

(22) Filed: Feb. 26, 2001

(65) Prior Publication Data

US 2002/0116983 A1 Aug. 29, 2002

(51) Int. Cl.$^7$ .................. G01N 33/497; G01N 27/02
(52) U.S. Cl. .................. 73/23.34; 422/82.02
(58) Field of Search ............... 73/23.34, 14.06; 324/71.1; 422/4, 82.02; 702/116; 438/99; 436/149

(56) References Cited

U.S. PATENT DOCUMENTS

| | | | |
|---|---|---|---|
| 3,831,432 A | | 8/1974 | Cox ........................... 73/23 |
| 3,999,122 A | * | 12/1976 | Winstel et al. ............ 324/71.1 |
| 4,730,479 A | | 3/1988 | Pyke et al. .................... 73/23 |
| 4,887,455 A | * | 12/1989 | Payne et al. ............... 73/24.06 |
| 5,159,661 A | | 10/1992 | Ovshinsky et al. ............ 706/33 |
| 5,200,634 A | * | 4/1993 | Tsukada et al. ............ 257/291 |
| 5,948,355 A | * | 9/1999 | Fujishima et al. .............. 422/4 |
| 6,033,601 A | * | 3/2000 | Persaud et al. .............. 252/500 |
| 6,042,788 A | * | 3/2000 | De Wit et al. ............ 422/82.02 |
| 6,085,576 A | | 7/2000 | Sunshine et al. ........... 73/29.01 |
| 6,207,472 B1 | * | 3/2001 | Callegari et al. ............. 438/99 |
| 6,236,951 B1 | * | 5/2001 | Payne et al. ................ 702/116 |
| 6,284,562 B1 | * | 9/2001 | Batlogg et al. ............... 438/99 |
| 6,319,724 B1 | * | 11/2001 | Lewis et al. ................ 436/149 |
| 2001/0026251 A1 | * | 10/2001 | Hunter et al. ................. 345/55 |
| 2001/0030323 A1 | * | 10/2001 | Ikeda .......................... 257/59 |

FOREIGN PATENT DOCUMENTS

| | | | | |
|---|---|---|---|---|
| DE | 29 47 050 A | 5/1981 | .......... | G01N/27/12 |
| DE | 3642891 A1 | 6/1988 | .......... | G01N/27/12 |

(List continued on next page.)

OTHER PUBLICATIONS

Patent Abstracts of Japan, Publication No. 05312746, (Abstract of JP Application 04113470), Publication Date: Nov. 22, 1993, "Bad–Smell Sensor".

Patent Abstracts of Japan, Publication No. 04181150, Nov. 15, 1990 (Abstract of JP Application No. 02309027), Publication Date: Jun. 29, 1992, "Lipid Film Type Odor Sensor".

(List continued on next page.)

Primary Examiner—Helen Kwok
Assistant Examiner—Jay L Politzer
(74) Attorney, Agent, or Firm—John F. McCabe

(57) ABSTRACT

An electronic odor sensor includes first and second amplifiers, a biasing network, and a device connected to receive the output signals from the first and second amplifiers. The device is configured to correlate the received output signals to the presence or absence of an odor. The first and second amplifiers have respective first and second organic semiconductor layers and are configured to produce output signals responsive to the conductivities of their respective organic semiconductor layers. The conductivities of the organic semiconductor layers are responsive to voltages applied to associated ones of the amplifiers and to the presence of the odor. The biasing network applies the voltages to the amplifiers.

21 Claims, 7 Drawing Sheets

FOREIGN PATENT DOCUMENTS

| | | | | |
|---|---|---|---|---|
| DE | 40 28 062 A | | 3/1992 | ......... G01N/27/414 |
| EP | 9600383 | * | 1/1996 | ......... G01N/27/12 |
| EP | 9600384 | * | 1/1996 | ......... G01H/27/12 |
| EP | 0175852 | * | 10/2001 | ............ G09G/3/32 |
| JP | 02228392 A | * | 1/1999 | |
| JP | 11019454 A | * | 9/1999 | |
| WO | 97/18467 | | 5/1997 | ......... G01N/33/00 |
| WO | WO 98/41853 A | | 9/1998 | ......... G01N/27/141 |
| WO | WO 99/08105 | | 2/1999 | ......... G01N/33/00 |
| WO | WO 99/61902 | | 12/1999 | ......... G01N/27/27 |

OTHER PUBLICATIONS

Ohmori, Y. et al: *Gas–Sensitive Schottky Gated Field Effect Transistors Utilizing Poly(3–alkylthiophene) Films*, Japanese Journal of Applied Physics, vol. 30, No. 7B, 1991, pp. L1247–L1249.

Assadi, A. et al: *Determination of Field–Effect Mobility of Poly (3–Hexylthiophene) Upon Exposure to $NH_3$, Gas*, Synthetic Metals, vol. 37, 1990, pp. 123–130.

* cited by examiner

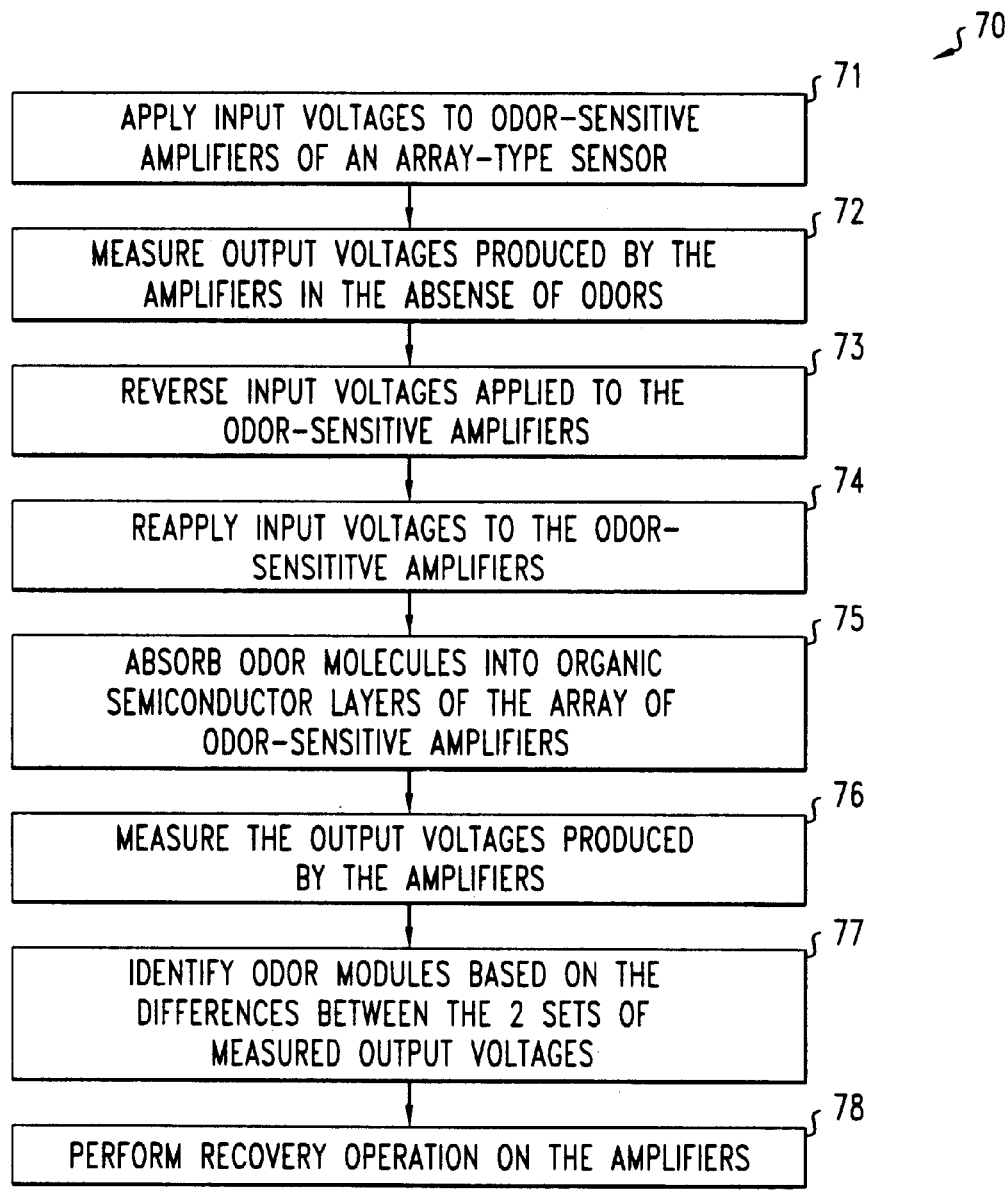

ELECTRONIC ODOR SENSOR

BACKGROUND OF THE INVENTION

1. Field of the Invention

This invention relates to electronic gas and chemical sensors.

2. Discussion of the Related Art

Sensors for gases and chemicals have applications in food processing, agriculture, medicine, and environmental surveillance. Herein, we refer to both gases and chemicals that sensors detect as odors. The applications of odor sensors depend on the sensors' selectivities, sensitivities, reproducibilities, and reliabilities. Some odor sensors have selectivities and sensitivities that enable both identifying odors and determining the concentrations of identified odor molecules.

Some odor sensors use resistors with resistances that are sensitive to the presence of specific odor molecules. In array-type resistance sensors, the resistances of individual ones of the sensitive resistors react differently to the presence of different types of odors. The resistors generate an array of resistance values that function as fingerprints for identifying various odors.

BRIEF SUMMARY OF THE INVENTION

In one aspect, the invention features an electronic odor sensor. The sensor includes first and second amplifiers, a biasing network, and a device connected to receive the output signals from the first and second amplifiers. The device is configured to correlate the received output signals to the presence or absence of an odor. The first and second amplifiers have respective first and second organic semiconductor layers and are configured to produce output signals responsive to the conductivities of their respective organic semiconductor layers. The conductivities of the organic semiconductor layers are responsive to voltages applied to associated ones of the amplifiers and to the presence of the odor. The biasing network applies the voltages to the amplifiers.

In a second aspect, the invention features an electronic odor sensor. The sensor includes first and second organic field-effect-transistors, a biasing network to cause voltages to be applied to gates of the first and second organic field-effect transistors, and a device connected to receive signals responsive to the drain currents in the transistors. The drain currents the transistors have values responsive to the presence of two odors when voltages are applied to the transistors. The device is also configured to distinguish between the presence of the first odor and the presence of the second odor based on values of the received signals.

In a third aspect, the invention features a process for detecting odors. The process includes absorbing an odor into organic semiconductor layers of an array of amplifiers and measuring output signals produced by the array of amplifiers in response to the act of absorbing. The layers have conductivities that respond differently to absorbing an odor, and the output signals are responsive to the conductivities of the layers. The process also includes determining the identity of the absorbed odor based on the measured set of output signals.

BRIEF DESCRIPTION OF THE SEVERAL VIEWS OF THE DRAWINGS

FIG. 8A is a flow chart for a process of identifying odors with the array-type electronic odor sensor of FIG. 6;

In the figures, like reference numbers refer to similar features.

DETAILED DESCRIPTION OF THE INVENTION

Herein, amplifiers include solid-state devices with active semiconductor layers, e.g., organic field-effect-transistors (OFETs) and/or bipolar transistors.

Figure 1:
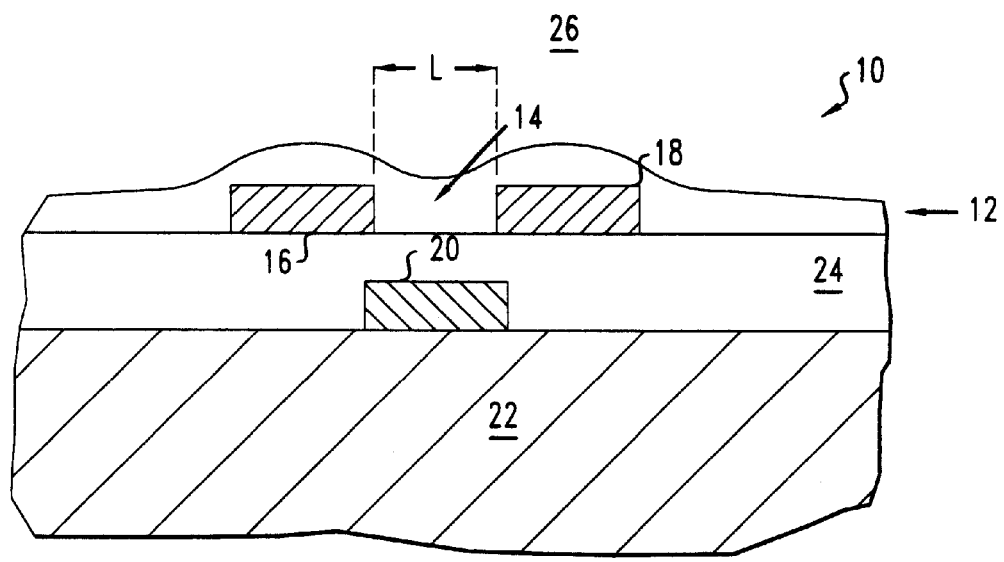
FIG. 1 is a cross-sectional view of an organic field-effect-transistor (OFET) that is sensitive to odors.

FIG. 1 is a cross-sectional view of an organic field-effect-transistor (OFET) 10 whose electrical properties are sensitive to the presence of odors. The OFET 10 has an organic semiconductor layer 12 with a thickness of about 10–100 nanometers (nm). The organic semiconductor layer 12 forms an outer covering of the OFET 10 and includes an active channel 14. The OFET 10 also includes source 16, drain 18, and gate 20. The gate 20 rests on a silicon substrate 22 and is insulated from the organic semiconductor layer 12, source 16, and drain 18 by a dielectric layer 24.

Herein, the active channel 14 refers to the portion of layer 12 located between the source 16 and drain 18. A voltage applied to gate 20 controls the conductivity of the active channel 14. The voltage on the gate 20 controls the conductivity of an active portion of the channel 14 adjacent to the dielectric layer 24, e.g., a few molecules thick. In some embodiments (not shown), the silicon substrate 22 also functions as the gate.

Since organic semiconductor layer 12 forms the outer covering of OFET 10, the channel 14 formed in the layer 12 is able to absorb odor molecules from ambient gas 26. Absorption of certain odor molecules changes the conductivity of active channel 14 by changing carrier densities, trap densities, mobilities, or another property of the organic semiconductor layer 12. Changing the channel's conductivity changes the drain current in the channel 14. Thus, changes in the drain current are electrical responses to the presence of odor molecules in ambient gas 26 above the unprotected layer 12 and characterize OFET 10 as an electronic odor sensor.

The odor-sensitivity of OFET 10 depends on both the physical structure and the chemical composition of active layer 12.

Organic semiconductor layer 12 has a polycrystalline structure in which grains have diameters of about 10–100 nm. These small grain sizes facilitate penetration of odor molecules into the layer 12 by making a high surface area available for odor penetration. These effects of small grain sizes facilitate chemical and/or physical interaction between odor molecules and molecules of active channel 14 and ordinarily increase the odor-sensitivity of the OFET 10.

The active layer 12 includes a stable organic semiconductor such as a material made of organic molecules with conjugated double bonds. Exemplary organic semiconductors include hydrocarbon-end-substituted α-sexithiophene (α-6T), hydrocarbon-substituted polymers of thiophene, 1,4,5,8-naphthalene tetracarboxylic dianhydride (NTCDA), copper phthalocyanine (CuPc), and a metal-hexadecafluorophthalocyanine ($F_{16}MPc$). Exemplary semiconductors based on α-6T include di-hexyl-α-6T (dHα6T), di-butyl-α-6T (dBα6T), di-dodecyl-α-6T (dDDα6T), and di-octadecyl-α-6T (dODα6T). Exemplary semiconductors based on polymers of thiophene include regioregular poly-hexyl-thiophene (pHT), poly-dodecyl-thiophene (pDDT), and poly-octyl-thiophene (pOT). The semiconductors based on $F_{16}MPc$ include molecules in which the metal atom "M" is copper, zinc, iron, or cobalt.

The odor-sensitivity of OFET 10 also depends on the types of hydrocarbon end-groups on molecules of organic semiconductor layer 12 and on the sizes of the odor molecules. Both of these properties affect penetration depths of the odor molecules into the active channel 14. If the active channel 14 is composed of molecules with larger hydrocarbon end-groups, the corresponding OFET 10 ordinarily has a higher sensitivity due to higher penetration of the odor molecules.

Figure 2:
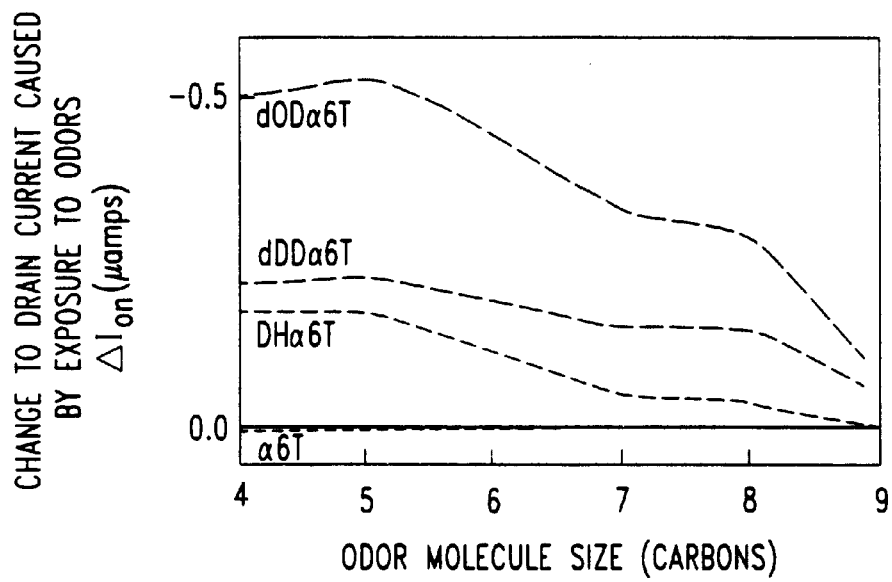
FIG. 2 illustrates how sensitivities of exemplary odor-sensitive OFETs depend on sizes of odor molecules.

FIG. 2 graphs the change to the drain current, i.e., $\Delta I_{on}$, which results from exposure to an odor, for OFETs 10 that have semiconductor layers 12 of different molecular compositions. The molecules of the different organic semiconductor layers 12 have different hydrocarbon end-groups. For OFETs 10 in which the active channel 14 is made of dODα6T, dDDα6T, and dHα6T, the responsiveness of the change to the drain current $\Delta I_{on}$ to presence of the alcohol odor molecules increases as lengths of the hydrocarbon end-groups of the molecules increase. Ordinarily, an OFET 10 is more sensitive to odor molecules if its organic semiconductor layer 12 includes molecules with larger hydrocarbon end-groups.

Figure 3:
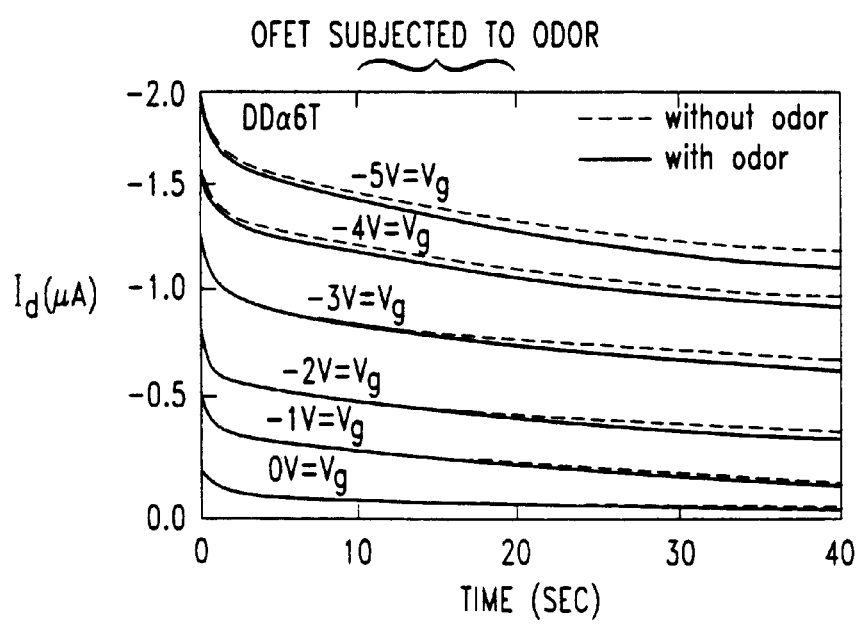
FIG. 3 illustrates the sensitivity of the drain current of the OFET of FIG. 1 to odors for various gate bias voltages.

The electrical properties of OFET 10 of FIG. 1 are time-dependent. FIG. 3 illustrates the time-dependence of the drain current $I_d$ as a function of time for various gate-source voltages $V_g$. The drain current $I_d$ depends on time even when odor molecules are not present. To illustrate the sensitivity of the OFET 10 to odors, FIG. 3 shows the drain current $I_d$ both for calibration periods in which odor molecules are absent and for test periods in which odor molecules are present. During the test periods, odor molecules of 1-octanol are present in ambient gas 26 and diffuse into the active channel 14 of dDα6T. In the test periods, ambient gas 26 carries 1-octanol molecules during a 10 second period that starts about ten seconds after OFET 10 is powered to produce a drain current.

After exposing OFET 10 to 1-octanol odor molecules, the value of the drain current $I_d$ starts to deviate from the value of the drain current for corresponding times in the calibration periods in which 1-octanol odor molecules are absent. The size of the deviation between the drain currents $I_d$ of the test and calibration periods depends on both the biasing voltage $V_g$ and the time that the OFET's semiconductor channel is exposed to the 1-octanol odor. For $V_g$ more negative than −1.0 volts, the deviation $\Delta I_d$ between the drain currents is measurable after about 5 seconds of exposure to the 1-octanol odor molecules. This delay is caused by the time it takes for 1-octanol molecules to diffuse into the organic semiconductor channel 14. For $V_g$>−1.0 volts, 1-octanol odor molecules do not cause a measurable deviation $\Delta I_d$ in the drain current $I_d$ from the value of the drain current $I_d$ in the absence of the 1-octanol odor molecules.

The deviation $\Delta I_d$ in drain current is an electrical response to the presence of odor molecules, i.e., presence of the odor molecules has altered the electrical properties of the OFET 10. The size of the response also depends on the gate-source voltage $V_g$.

Figure 4:
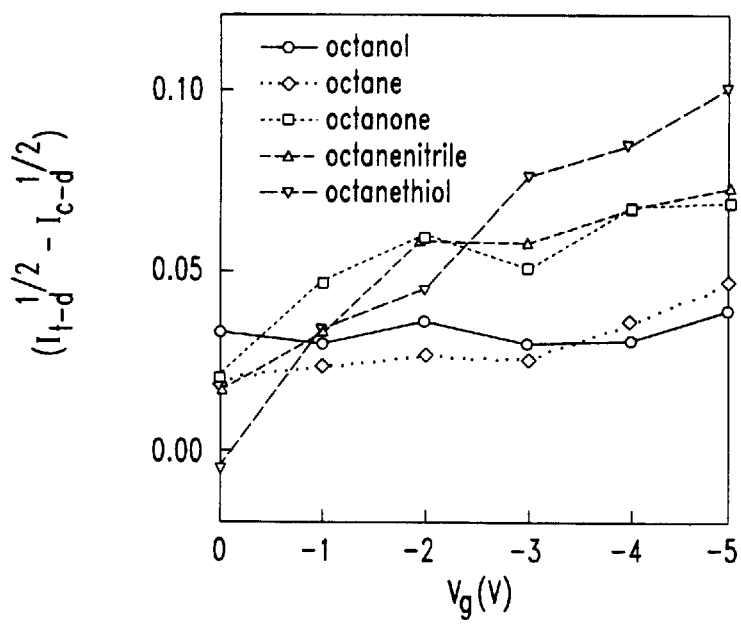
FIG. 4 illustrates the odor-sensitivity of the OFET of FIG. 1 to different odors as a function of the gate bias voltage.

FIG. 4 shows how the drain current of OFET 10 with an uncovered semiconductor layer 12 of dDDαT deviates in response to the presence of various odor molecules for different values of the gate-source voltages $V_g$. The deviations are measured through the difference $I_{t-d}^{1/2}-I_{c-d}^{1/2}$ where $I_{t-d}$ and $I_{c-d}$ are values of the drain current $I_d$ during equivalent temporal intervals of the respective calibration and test periods. During the calibration period, the OFET 10 is not exposed to the odor. During the test period, the OFET 10 is exposed to the odor, and the drain current is measured after a 5-second exposure of the OFET 10 to the odor. The difference $I_{t-d}^{1/2}-I_{c-d}^{1/2}$ vanishes for odors that do not produce a response in electrical properties of the OFET 10.

The measurements of FIG. 4 illustrate that relative responses of the drain current to various odors are also affected by gate-source voltage $V_g$. For example, while the presence of octanethiol odor molecules does not affect the value of the drain current of the OFET 10 when $V_g$ is zero, a significant deviation in the drain current is observed when $V_g$ is more negative than −3 volts. The set of values of $I_{t-d}^{1/2}-I_{c-d}^{1/2}$ that corresponds to a set of values of the gate-source voltages, e.g., for $\{V_g\}=(-0, -1.0, -2.0, -3.0, -4.0)$, provides a vector-valued "fingerprint". The set values of $I_{t-d}^{1/2}-I_{c-d}^{1/2}$ is a fingerprint, because the set of values is usable to identify and distinguish between the presence of the different odor molecules listed in FIG. 4. The set of values of $I_{t-d}^{1/2}-I_{c-d}^{1/2}$ are different for different odor molecules, because sensitivities of organic semiconductor layer 12 to odors vary when biased by different gate voltages $V_g$.

Furthermore, the set of values of $I_{t-d}^{1/2}-I_{c-d}^{1/2}$ may be normalized. To perform the normalization, the set of values of $I_{t-d}^{1/2}-I_{c-d}^{1/2}$ is divided by the value of $I_{t-d}^{1/2}-I_{c-d}^{1/2}$ for a preselected $V_g$, e.g., for $V_g=-5.0$. This type of normalization produces a vector-object that identifies an odor in a manner that does not depend on the concentration of the odor molecules. For such a vector, the pattern formed by the magnitudes of the components distinguishes between different types of odor molecules.

Figure 5:
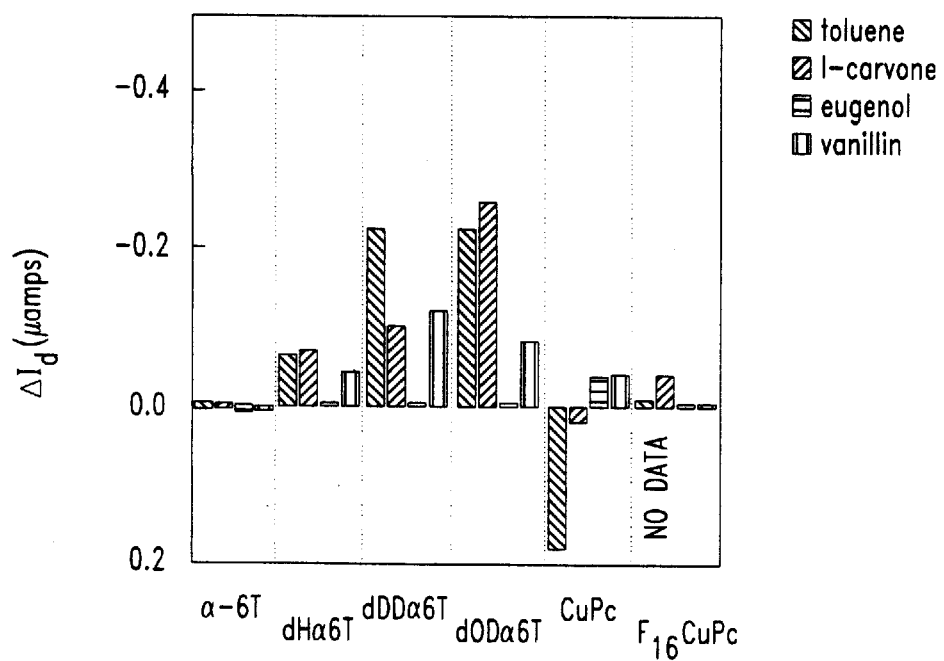
FIG. 5 shows output signals responsive to different odors from OFETs that have active channels with different compositions.

FIG. 5 shows deviations to drain currents, i.e., $\Delta I_d=I_{t-d}-I_{c-d}$, caused by diffusion of various types of odor molecules into active layers 12 of different composition. The various odor molecules cause different deviations in the drain currents $I_d$ for OFETs 10 with active layers of different compositions. Thus, an array of OFETs 10 with active layers 12 of different compositions respond to exposure to odors by a set of drain current deviations $\Delta I_d$, and the set of $\Delta I_d$'s identify and distinguish between the odors. For example, the array of drain current deviations $\Delta I_d$ for OFETs 10 whose active layers 12 comprise dHα6T, dDDα6T, dODα6T, and CuPc provides a vector-like set of current deviations that identifies and distinguishes between toluene, 1-carvone, eugenol, and vanillin.

Herein, an object identifies and distinguishes between the presence of first and second odors if the object has a value associated with the first odor and a value associated with the second odor and the two values are different. For example, one such object is orientation of the 5-dimensional vector of values of $\Delta I_d$ produced by OFETs with dHα6T, dDDα6T, dODα6T, and CuPc active channels 14.

Figure 6:
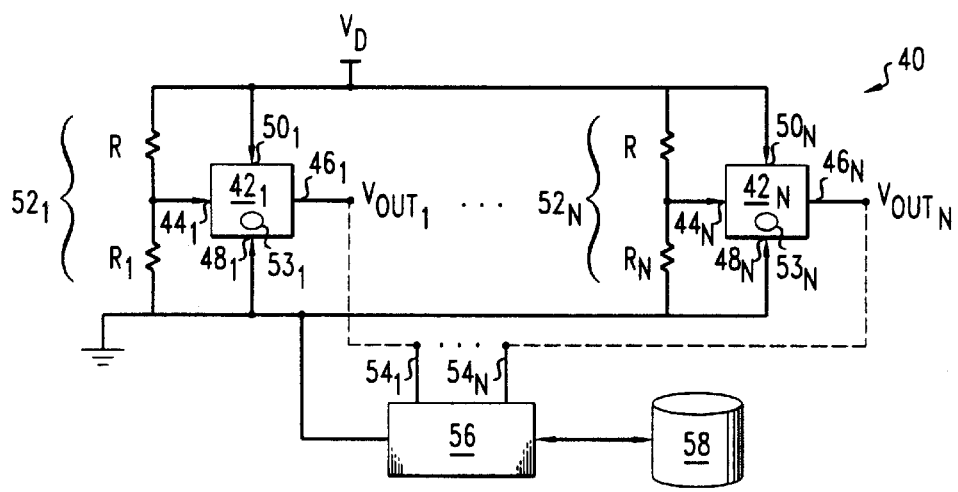
FIG. 6 shows an array-type electronic odor sensor.

FIG. 6 shows an electronic array-type odor sensor 40. The array-type sensor 40 includes N odor-sensitive voltage amplifiers 42$_1$–42$_N$ having respective input terminals 44$_1$–44$_N$, output terminals 46$_1$–46$_N$, and power terminals 48$_1$–48$_N$, 50$_1$–50$_N$. The input terminals 46$_1$–46$_N$ connect to voltage divider circuits 52$_1$–52$_N$ that apply input voltages to the amplifiers 42$_1$–42$_N$. These input voltages may be DC or pulsed. The output terminals 46$_1$–46$_N$ connect to input terminals 54$_1$–54$_N$ of a comparator device 56, which measures the output voltages $V_{out-1}$–$V_{out-N}$ and determines the identity of an odor from the measured values of the output voltages $V_{out-1}$–$V_{out-N}$.

The array-type sensor 40 performs parallel accumulation and analysis of the set of output voltages $V_{out-1}$–$V_{out-N}$, which are used to identify and distinguish between odors. Accumulating the set of output voltages in parallel speeds up odor detection, because the measurement process for individual output voltages involves test periods that are from about 1 to about 40 seconds long.

The different amplifiers 42$_1$–42$_N$ have organic semiconductor layers 53$_1$–53$_N$ with field-induced conductivities that respond differently to the presence of odors. The set of output voltages $V_{out-1}$–$V_{out-N}$ from the amplifiers 42$_1$–42$_N$, also responds to the conductivities of the layers 53$_1$–53$_N$. Due to differences between responses of the conductivities of the layers 53$_1$–53$_N$ to different odors, the set of output voltages $V_{out-1}$–$V_{out-N}$ takes different values for different odors. The conductivities of the layers 53$_1$–53$_N$ also respond to the values of the input voltages applied to input terminals 44$_1$–44$_N$.

The set of output voltages $V_{out-1}$–$V_{out-N}$ forms an N-dimensional vector whose direction in N-dimensional space identifies and distinguishes between different odors due to the differences in the responses of the conductivities of layers 53$_1$–53$_N$ to the odors. The comparator device 56 compares the set of N output voltages $V_{out-1}$–$V_{out-N}$ to reference sets of output voltages for matches. The values of the reference sets correspond to the output voltages $V_{out-1}$–$V_{out-N}$ generated by the amplifiers 42$_1$–42$_N$ in response to the presence of known odors. A data storage device 58 connected to the comparator device 56 stores the values of the reference sets. Exemplary data storage devices 58 include an active memory, a magnetic disk, or an optical disk.

Exemplary comparator devices 56 include a computer that executes a software program, e.g., a computer executable program stored on an optical or magnetic disk. The program performs a process for measuring the set of output voltages $V_{out-1}$–$V_{out-N}$ at terminals 54$_1$–54$_N$, comparing the measured set of output voltages to reference sets stored in the data storage device 58, and determining the identity of an odor molecule from the comparison.

Figure 7A:
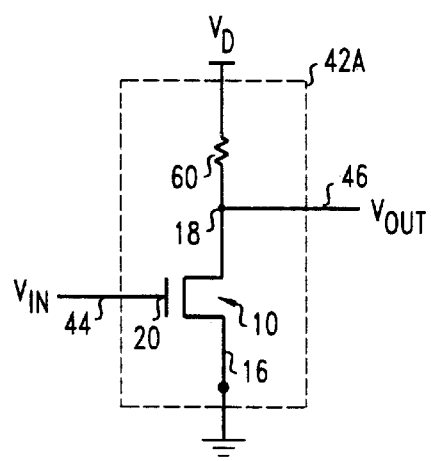
FIGS. 7A and 7B show alternate odor-sensitive amplifiers for use in the array-type electronic odor sensor of FIG. 6.

FIG. 7A shows an exemplary voltage amplifier 42A for use as odor-sensitive amplifiers 42$_1$–42$_N$ of FIG. 1. In the amplifier 42A, odor-sensitive OFET 10 of FIG. 1 and load resistor 60 form a series circuit between $V_D$ and ground voltage sources. The OFET's gate 20 and drain 18 connect to respective input and output terminals 44, 46. The input voltage $V_{IN}$ biases the OFET 10, and the OFET's drain voltage is the output voltage $V_{OUT}$ of the amplifier 42A. The output voltage $V_{OUT}$ is responsive to the conductivity of the OFET's active channel, i.e., channel 14 of FIG. 1. The conductivity is responsive both to the presence of odors in ambient gas 26 and to the voltage $V_{IN}$ at input terminal 44. Thus, the value of the drain voltage $V_{OUT}$ and drain current of the OFET 10 are responsive to the presence of odors.

Figure 7B:
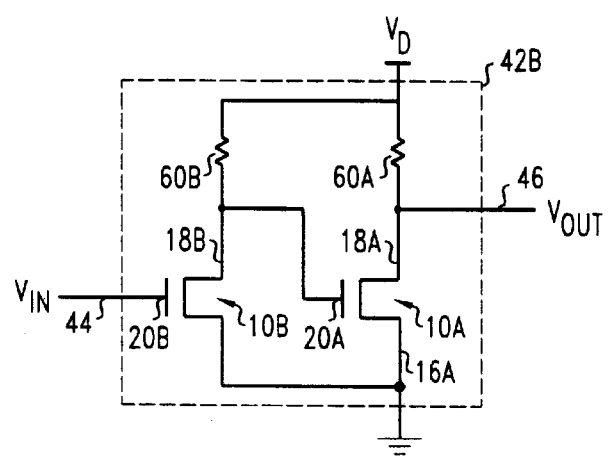

FIG. 7B shows an alternate voltage amplifier 42B for use as odor sensitive amplifiers 42$_1$–42$_N$ of FIG. 6. The amplifier 42B has two cascaded stages. Each stage includes a load resistor 60A, 60B connected in series with a drain or source of an odor-sensitive OFET 10A, 10B. The stages connect between $V_D$ and ground voltage sources. The OFET 10B of the first stage has a gate 20B biased by voltage $V_{IN}$ at input terminal 44, i.e., input terminals 44$_1$–44$_N$ in FIG. 6, and a drain 18B that biases the gate 20A of the OFET 10A of the second stage in a cascade-like configuration. The drain 18A of the OFET 10A of the second stage connects to output terminal 46 of the amplifier 42B. Both OFETs 10A, 10B have organic semiconductor channels with conductivities that are responsive to the input voltage $V_{IN}$ and to the presence of odors in ambient gas. The cascaded arrangement of the odor-sensitive OFETs 10A, 10B makes the output voltage $V_{OUT}$ more sensitive to odors, because the output voltage of the odor-sensitive first stage is amplified by the odor-sensitive second stage.

Herein, the voltage gain of the odor sensitive amplifiers, e.g., amplifiers 42A and 42B of FIGS. 7A and 7B, are not essential. Some exemplary amplifiers have voltage gains greater than 1 and other exemplary amplifiers have voltage gains less than or equal to 1.

Referring again to FIG. 6, the odor-sensitive amplifiers 42$_1$–42$_N$ have different sensitivities to various odors so that the output voltages $V_{out-1}$–$V_{out-N}$ provide a pattern of voltage values for distinguishing between different odors. In some sensors 40, the different sensitivities of the amplifiers 42$_1$–42$_N$ result from different biasing voltages applied at input terminals 44$_1$–44$_N$. To produce different biasing voltages, the N voltage divider circuits 52$_1$–52$_N$ have resistors $R_1$–$R_N$ with different values. In other sensors 40, the different sensitivities of the amplifiers 42$_1$–42$_N$ result from using OFETs 10 in different ones of the amplifiers 42$_1$–42$_N$. In those sensors, the different OFETs 10 have active channels 14 with either different organic semiconductors, different grain sizes, or different channel depths, i.e., different thicknesses of organic semiconductor layer 12 of FIG. 1.

Figure 8B:
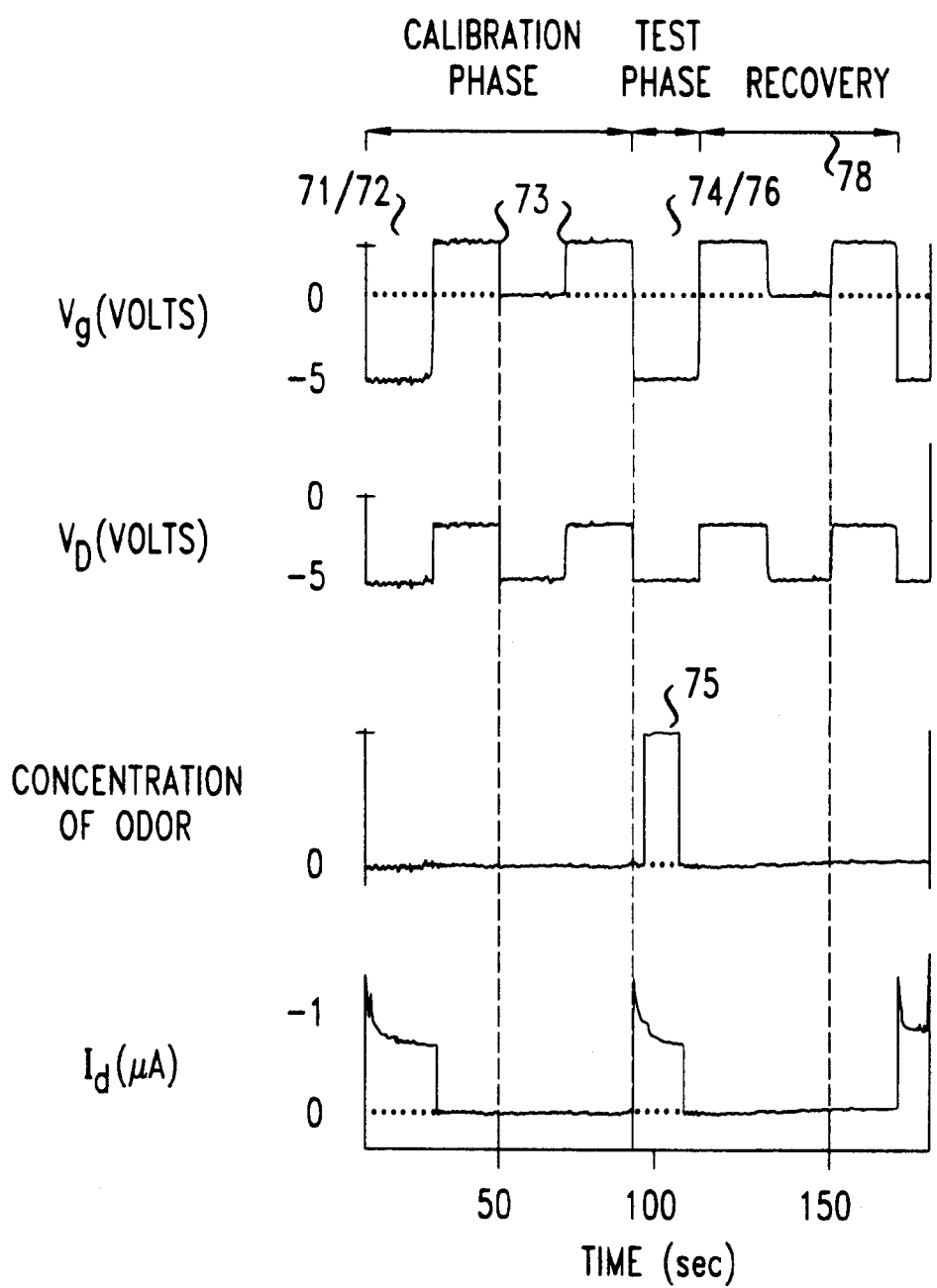
FIG. 8B shows gate and drain voltages applied to an OFET and drain currents measured through the OFET during a sniffing cycle of the process of FIG. 8A.

FIG. 8A is a flow chart for a process 70 that identifies odor molecules using an electronic array-type odor sensor 40 of FIG. 6. The process 70 has a calibration phase and a test phase. During the calibration phase, the process 70 includes applying selected input voltages to and powering the odor-sensitive amplifiers 42$_1$–42$_N$ that generate sets of output voltages $V_{OUT-1}$–$V_{OUT-N}$ responsive to small changes in the input voltages (step 71). For some embodiments, the selected input voltages applied to the odor-sensitive amplifiers 42$_1$–42$_N$ have different values so that the individual amplifiers 42$_1$–42$_N$ have different sensitivities to odor molecules. After powering the amplifiers 42$_1$–42$_N$, the process 70 includes measuring the output voltages without subjecting the odor-sensitive amplifiers 42$_1$–42$_N$ to odor molecules (step 72). After measuring the output voltages, the process 70 includes reversing the input voltages so that the output voltages from odor-sensitive amplifiers 42$_1$–42$_N$ are freed of effects of the previous input voltages (step 73). For the odor-sensitive amplifiers 42A, 42B of FIGS. 7A and 7B, reversing the input voltages causes the conductivities of active channels 14 of the OFETs 10, 10A, 10B to recover to pretest initial values for a given bias condition. In response to applying the reversed input voltages, carrier densities in the active channels 14 become low as previously trapped charge carriers are freed from the channels 14. During the test phase, the process 70 includes again powering the odor-sensitive amplifiers $42_1$–$42_N$ and reapplying the same selected input voltages to the amplifiers $42_1$–$42_N$ (step 74). At a preselected time thereafter, the process 70 includes passing gas, which carries odor molecules, over the odor-sensitive amplifiers $42_1$–$42_N$ so that the odor molecules are absorbed into active layers 14 therein (step 75). With the same delay after applying input voltages to and powering the amplifiers $42_1$–$42_N$ as used in step 72, the process 70 includes measuring the output voltages produced by the odor-sensitive amplifiers $42_1$–$42_N$ (step 76). The process 70 includes using differences between the output voltages measured during the test and calibration phases to identify the odor molecules present and to determine concentrations of the odor molecules (step 77). By basing odor sensing on the differences between the output voltages measured in the calibration and test phases, background effects such as the drain current drift shown in FIG. 3 are eliminated.

After the calibration and test phases, the process 70 includes performing a recovery operation that reinitializes the odor-sensitive amplifiers for another sensing cycle with a new odor (step 78). In one embodiment, the recovery operation includes passing odor-free gas over the amplifiers $42_1$–$42_N$ to outgas odor molecules bound in the organic semiconductor channels 14 and reversing input voltages to the odor-sensitive amplifiers $42_1$–$42_N$ during the outgasing as previously described. Some embodiments heat amplifiers $42_1$–$42_N$ to about 100° C. to outgas odor molecules during the recovery operation. After the recovery operation, the carrier densities and chemical composition of the odor-sensitive organic semiconductor layers of the amplifiers $42_1$–$42_N$ are returned to their initial state. Then, the odor sensor 40 is ready to perform another sensing cycle for a new odor.

FIG. 8A illustrates an exemplary operation cycle of process 70 of FIG. 8A. The cycle includes a calibration phase, a test phase, and a recovery operation. During portions of the cycle, gate-source voltages $V_g$, drain-source voltages $V_D$, drain currents $I_d$, and concentrations of odor molecules are shown.

Figure 9:
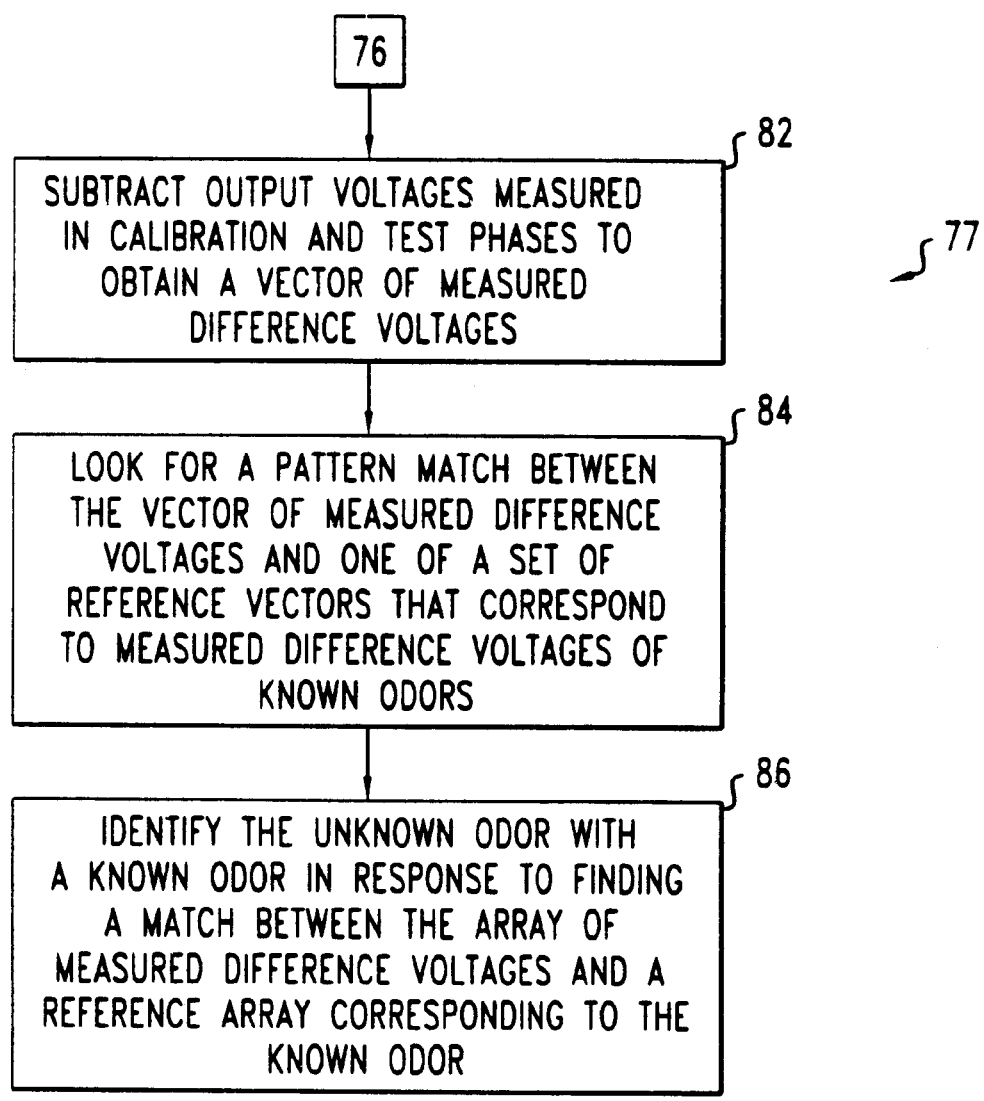
FIG. 9 is a flow chart for a process that identifies an odor from output voltages measured in the array-type odor sensor of FIG. 6.

FIG. 9 is a flow chart for the step 77 in which odor molecules are identified based on the measured output voltages. In the array-type sensor 40 of FIG. 6, comparator device 56 performs the identification step.

To perform the identification, the comparator device 56 forms a vector-like set of measured difference voltages by subtracting the set of output voltages measured in the calibration phase from the set of output voltages measured in the test phase (step 82). The components of the vector of measured difference voltages are indicative of changes to the array of amplifiers $42_1$–$42_N$, which are caused by the presence of odors. The comparator device 56 looks for a match between the vector of measured difference voltages and reference vectors of difference voltages that correspond to known odor molecules (step 84). The values of the reference vectors of difference voltages are stored in data storage device 58 of FIG. 6. To find a match, the comparator device 56 performs a pattern recognition algorithm that signals a match in response to two compared N-component vectors pointing in the same direction in N-dimensional space, i.e., up to a preselected error. The pattern recognition algorithm is capable of signaling a match between vectors with different lengths. In response to finding a match, between the set of measured difference voltages and one of the reference sets, the comparator device 56 identifies the odor detected by the array-type sensor 40 as the known odor corresponding to the matching reference set (step 86). The comparator device 56 also determines the concentration of the odor by comparing values of one component of the set of measured difference voltages and to the same component of the matching reference set. Since the measured voltage differences are proportional to the concentration of odor molecules, the ratio of the value of one measured component to the value of the same component for the matching reference set measures the concentration of odor molecules.

Referring again to FIG. 1, different embodiments of OFET 10 have active channels 14 whose physical dimensions, i.e., wide and length, have widely different sizes. For example, some OFETs 10 have a channel 14 whose length L that is less than 20 nanometers. For such a small channel length L, the response of the OFET can be more directly related to interactions between the organic semiconductor and analyte molecules. This may improve the sensitivity of an analyte sensor that uses such OFETs 10 as compared to a sensor that uses OFETs 10 with much longer channels.

Other embodiments of the invention will be apparent to those skilled in the art in light of the specification, drawings, and claims of this application.

What is claimed is:

1. An electronic odor sensor, comprising:
   a first amplifier having a first odor-sensitive organic semiconductor layer and being configured to produce an output signal responsive to the conductivity of the first organic semiconductor layer;
   a second amplifier having a second odor-sensitive organic semiconductor layer and being configured to produce an output signal responsive to the conductivity of the second organic semiconductor layer;
   a biasing network to apply a voltage to the first organic semiconductor layer and to apply a different voltage to the second organic semiconductor layer, the applied voltages to cause the conductivities of the layers to have different relative sensitivities to two odors; and
   a device connected to receive the output signals from the first and second amplifiers for the different applied voltages and configured to correlate the received output signals to the presence or absence of one of the odors.

2. The electronic odor sensor of claim 1, wherein the amplifiers comprise odor-sensitive organic transistors having one of sources and drains connected to the device.

3. The electronic odor sensor of claim 2, wherein the organic transistors have gates connected to receive the voltages applied to the associated organic semiconductor layers.

4. The electronic odor sensor of claim 2, wherein first and second ones of the organic transistors have active channels that include first and second organic semiconductors, respectively.

5. The electronic odor sensor of claim 2, wherein the network is configured to cause one voltage to be applied to a gate of the transistor of one of the amplifiers and a different voltage to be applied to a gate of the transistor of another of the amplifiers.

6. The electronic odor sensor of claim 2, wherein the organic transistors have active channels, the active channel of one of the organic transistors having a different depth than the active channel of another of the organic transistors.

7. The sensor of claim 2, wherein the organic transistors have active channels, a grain size of material of the active channel of one of the organic transistors being different than a grain size of material of the active channel of another of the organic transistors.

8. The electronic odor sensor of claim 2, wherein the amplifiers comprise other odor-sensitive organic transistors whose gates are coupled to receive the voltages applied to the associated amplifiers and whose one of sources and drains are connected to gates of the other organic transistors of the associated amplifiers.

9. The electronic odor sensor of claim 2, wherein the device is configured to identify the odor as a known odor in response to finding a match between values of the received set of output signals and values of a reference set of signals that corresponds to the set of output signals produced by the amplifiers in response to presence of the known odor.

10. The electronic odor sensor of claim 9, further comprising:
a data storage device connected to the device and configured to store a plurality of the reference sets of signals for comparing to the received output signals.

11. The electronic odor sensor of claim 2, wherein the network includes a first voltage divider connected to apply a first voltage to the first organic semiconductor layer and a second voltage divider connected to apply a second voltage to the second organic semiconductor layer.

12. A process for detecting odors, comprising:
absorbing an odor into odor-sensitive organic semiconductor layers of an array of amplifiers, each amplifier having an associated one of the layers;
applying different voltages across first and second ones of the layers to cause conductivities of the first and second ones of the layers to respond differently to absorption of first and second odors;
measuring a set of output signals produced by the amplifiers of the array in response to the act of absorbing an odor for the applied different voltages, the output signals being responsive to the conductivities of the layers; and
determining the identity of the absorbed odor based on the measured set of output signals.

13. The process of claim 12, wherein the applying causes the first and second layers to have different responses to absorption of the first odor and absorption of a second odor.

14. The process of claim 12, wherein the determining comprises comparing the measured set of output signals to reference sets of output signals corresponding to the sets of output signals produced by the amplifiers in response to absorptions of known odors.

15. The process of claim 14, wherein the amplifiers comprise odor-sensitive transistors and the applying applies different voltages to gates of respective first and second ones of the odor-sensitive transistors.

16. The process of claim 15, wherein the measuring includes receiving a set of signals indicative of drain currents in the first and second ones of the odor-sensitive transistors.

17. The process of claim 12, wherein the act of absorbing comprises generating, in parallel, the output signals from the amplifiers associated with the first and second ones of the layers.

18. The process of claim 12, further comprising:
performing a recovery operation that causes the organic semiconductor layers to release absorbed odor molecules in response to finishing the measuring.

19. The process of claim 18, wherein the performing a recovery operation includes applying a voltage that reverses a bias across at least one of the organic semiconductor layers.

20. The process of claim 18, wherein the performing a recovery operation includes heating the amplifiers.

21. The process of claim 18, wherein the performing a recovery operation includes passing analyte-free gas over the organic semiconductor layers.

* * * * *